United States Patent [19]
Gnezda et al.

[11] Patent Number: 5,935,861
[45] Date of Patent: Aug. 10, 1999

[54] DIAZONIUM ION ASSAY REAGENTS AND METHODS FOR THEIR USE

[75] Inventors: Matthew F. Gnezda, Fishers; Tracey E. Gordon, Noblesville; Jennifer S. Bournique; Sharanpal K. Walker, both of Indianapolis, all of Ind.

[73] Assignee: Boehringer Mannheim Corporation, Indianapolis, Ind.

[21] Appl. No.: 08/975,796

[22] Filed: Nov. 21, 1997

[51] Int. Cl.$^6$ .................................................. G01N 33/00
[52] U.S. Cl. ............................ 436/97; 436/8; 436/12; 436/166; 252/408.1
[58] Field of Search .................... 436/8, 12, 97, 436/164, 166, 169, 174, 903; 252/408.1

[56] References Cited

U.S. PATENT DOCUMENTS

| | | | |
|---|---|---|---|
| 2,854,317 | 9/1958 | Free et al. | 436/97 |
| 3,814,586 | 6/1974 | Fraser, Jr. et al. | 436/97 |
| 4,468,467 | 8/1984 | Babb et al. | 436/97 |
| 4,482,489 | 11/1984 | DiPippo | 534/556 |
| 4,530,724 | 7/1985 | Ueno et al. | 106/402 |
| 4,892,833 | 1/1990 | Weiss et al. | 436/97 |
| 4,902,477 | 2/1990 | Katsuyama et al. | 422/56 |
| 4,965,210 | 10/1990 | Modrovich | 436/97 |
| 5,026,831 | 6/1991 | Jung et al. | 534/752 |
| 5,071,623 | 12/1991 | Akutsu | 422/56 |
| 5,278,073 | 1/1994 | Grandjean | 436/12 |
| 5,493,011 | 2/1996 | Jung et al. | 534/751 |

FOREIGN PATENT DOCUMENTS

| | | |
|---|---|---|
| 1293676 | 12/1991 | Canada. |

OTHER PUBLICATIONS

Thomas et al. *Journal of Pharmacy & Pharmacology*, vol. 14, No. 9, pp. 587–596, Sep. 1962.

Chin-Chun Chen et al., "Sulfanilamide for the determination of total bilirubin" *Clin. Chem.* (1980) 26:990.

Doumas and Wu, "The measurement of bilirubin fractions in serum" *Critical Reviews in Clinical Laboratory Sciences* (1991) 28:415–445.

Doumas et al., "Candidate reference method for determination of total bilirubin in serum: Development and validation" *Clin. Chem.* (1985)31(11):1779–1789.

Inukai, Yoshihiko, "Reaction product of poly(ethyl vinylmalonate) and aniline, and polymeric azo dyes derived from the product" *Nippon Kagaku Kaishi* (1972)3:654–658. (Abstract of article included herewith, DIALOG® No. 77(12)76644y) (2 pages total).

Kumashiro et al., "Preparation of 2–methyl–5–nitrophenol by hydrolysis of 2–methyl–5–nitrobenzenediazonium sulfate" Japanese Patent No. 09132549 (May 20, 1997). (Abstract of Japanese Patent included herewith, DIALOG® No. 127(4)50389) (2 pages total).

Lott and Doumas, "'Direct' and total bilirubin tests: Contemporary problems" *Clin. Chem.* (1993) 39(4):641–647.

Malloy, H., "The determination of bilirubin with the photoelectric colorimeter" *J. Biol. Chem.* (1939) 119:481–490.

Michaelsson, M., *Scand. J. Clin. Lab. Invest.* (1961) 13(Suppl.)1–80.

Shihabi, Z.K., et al., "A modified malloy–evelyn procedure for total bilirubin in microsamples" *Amer. J. Med. Tech.* (1977) 43(10):1004–1007.

Zollinger, Heinrich, "Methods for the preparation of aromatic and heteroaromatic diazo compounds" *Diazo Chemistry I, Aromatic and Heteroaromatic Compounds* VCH Publishers, New York, NY 1994, Chapter 2.

*Primary Examiner*—Maureen M. Wallenhorst
*Attorney, Agent, or Firm*—Morrison & Foerster LLP

[57] ABSTRACT

Diazonium ions which are useful as reagents for the assay of bilirubin content in a sample, such as a body fluid sample, are provided. In one preferred embodiment, 2-methyl-3-nitroaniline diazonium ion is provided, having the structure:

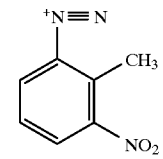

Also provided are reagent compositions including the diazonium ions. The reagent compositions may be in liquid or solid form, and further may include other components, such as buffers, carriers, and solubilizers. Salts including the diazonium ion and a counteranion also are provided. Also provided are methods of using the diazonium ions in assays to detect or quantitate bilirubin present in a sample such as a body fluid sample. Using the assays, the amount of direct, indirect, and total bilirubin in a sample may be accurately and reproducibly detected, and optionally correlated with the presence or absence of any of a variety of diseases or disorders of organs such as the liver, gall bladder or intestines. Using the assays, a wide range of different body fluid samples, such as urine, plasma or serum samples may be tested, and the interference in the assay from other components of the sample may be minimized.

35 Claims, 1 Drawing Sheet

DIAZONIUM ION ASSAY REAGENTS AND METHODS FOR THEIR USE

TECHNICAL FIELD

This invention relates to stable diazonium ion compounds, and methods for their use in conducting assays for the detection and quantitative analysis of bilirubin in plasma, blood or other samples.

BACKGROUND ART

Bilirubin is a principal component of bile pigment in body fluid. Bilirubin present in serum is a product of the decomposition of heme originating from hemoglobin in red blood cells. Two fractions of bilirubin are present in blood serum, unconjugated and conjugated bilirubin. Conjugated bilirubin is bilirubin which is conjugated with glucuronic acid in the liver and rendered water soluble. The conjugated bilirubin also is referred to as "direct" bilirubin, and the bilirubin not conjugated with glucuronic acid is referred to as "indirect" bilirubin or unconjugated bilirubin. Normally, only small amounts of bilirubin are found in the blood, the normal concentration being for direct bilirubin up to about 0.25 mg/l 100 ml serum ($\leq 4.3$ μmol/L); and for indirect bilirubin up to about 0.75 mg/100 ml serum ($\leq 12.7$ μmol/L). The content of bilirubin in blood increases with an increase in decomposition of hemoglobin and a decrease in liver function.

The determination of both bilirubin fractions is of importance in medical diagnosis. Normally, bilirubin is excreted from the gall bladder with the biliary fluid into the intestine. However, this mechanism is disturbed in various disease states. Thus, for example, in the case of increased hemoglobin breakdown, the bilirubin conjugation system can be overloaded so that the ratio of direct/indirect bilirubin is changed. In the case of liver cell damage, disturbances of the outflow in the biliary capillary or bile duct obstructions, the excretion of the bilirubin via the gall bladder into the intestine is reduced or completely blocked. This leads to increased bilirubin concentrations in the blood. The absolute concentration of the bilirubin and the ratio of direct/indirect bilirubin can thereby be influenced. Thus, from the measurement of both values, important diagnostic conclusions can be made regarding the nature and localization of certain diseases of the liver, gall bladder and intestinal tract. Generally, the total bilirubin is usually determined first, and then the direct bilirubin content is measured. The indirect bilirubin portion is obtained from the difference between the two values. Methods for measuring serum bilirubin are reviewed in Doumas and Wu, *Critical Reviews in Clinical Laboratory Sciences*, 28:415–445 (1991); and Lott and Doumas, *Clin Chem.*, 39:641–647 (1993), the disclosures of which are incorporated herein.

Analytical tests which permit the quantitative analysis of bilirubin are very useful clinically. The most widely used assay for bilirubin has been the so called diazo method. In the diazo method, a sample suspected of containing bilirubin is contacted with a reagent composition which includes a diazonium salt. The diazonium salt reacts with bilirubin to form two azobilirubin fragments. The azobilirubin has an extinction coefficient which is higher than that of bilirubin itself and is easily detectable.

Many diazonium salts have been used in the diazo method for determining bilirubin. For example, diazotized sulfanilic acid couples with bilirubin to give a yellow diazobilirubin pigment. Details of the diazo method for quantitative analysis of bilirubin are described in Doumas et al., *Clin Chem.*, 31:1779–1789 (1985); M. Michaelsson, *Scand. J. Clin. Lab. Invest.*, 13 (Suppl.), 1–80 (1961); H. Malloy, *J. Biol, Chem.*, 119, 481(1939); and Z. K. Shihabi, et al., *American Journal of Medical Technology*, 43(10), 1004–1007 (1977), the disclosures of which are incorporated herein. Other diazonium salts, such as 2,4- and 2,5-dichlorophenyldiazonium salts, have been used for the detection of bilirubin in serum and urine. However, methods using these diazonium salts are known to be relatively insensitive, and some of these diazonium salts, when dry, are explosively unstable, i.e., subject to shock induced decomposition. U.S. Pat. No. 4,468,467 to Babb et al. Another diazonium compound which has been used for the determination of bilirubin is diazotized sulfanilamide. Chin-Chung Chen et al., *Clin Chem.*, 26:990 (1980). Synermed™ (Synermed, Inc., Quebec, Canada) total bilirubin reagent is commercially available which includes a stabilized diazonium salt of 3,5-dichloroaniline, 3,5-dichlorophenyl diazonium tetrafluoroborate, which reacts with bilirubin to form azobilirubin which absorbs maximally at 540 nm. The red azobilirubin formed can be shifted to a blue color which absorbs at 600 nm upon the addition of alkali. Caffeine and surfactants are used as reaction accelerators.

U.S. Pat. No. 4,468,467 to Babb et al. describes certain substituted sulfanilamide and carbonamide diazonium salts for bilirubin assays. U.S. Pat. No. 4,902,477 to Katsuyama et al. discloses an analytical element for quantitative analysis of bilirubin by a diazo method, which includes certain aryldiazonium salts having in the aryl group a substituent which is an alkoxycarbonyl group, an alkylaminosulfonyl group or an alkylaminocarbonyl group. U.S. Pat. No. 4,892,833 to Weiss et al. discloses aryldiazonium salts wherein the aryl group is substituted with halogen groups and lower alkoxy groups for use in the determination of bilirubin.

Many of the assay reagents used in current assays have problems associated with their use. For example, in the case of automated bilirubin assays using a commercially available dichloroaniline diazonium tetrafluoroborate salt, the diazonium form of the chloroaniline derivatives is known to interact strongly with indican, a compound found in the serum of renal dialysis patients making it unsuitable for this sample type. Hemolyzed samples also cannot be used in many of the assays due to extensive interference by hemoglobin. Some of the reagents have a relatively low solubility in aqueous systems, thus reducing their usefulness in these systems. Additionally, many of the reagents are unstable in the liquid form, cannot be readily transported, and do not have a useful shelf-life.

It is an object of the invention to provide diazonium ion compounds which can be used as assay reagents for the detection of bilirubin in body fluid samples. It is a further object of the invention to provide diazonium ion compounds which are thermally stable making long distance shipping more feasible. It is yet another object of the invention to provide diazonium ion compounds which are thermally stable, have a long term shelf-life, and may be stored while retaining activity, for example, for periods of one year or more.

DISCLOSURE OF THE INVENTION

Diazonium ions which are useful as reagents for the assay of bilirubin content in a sample, such as a body fluid sample, are provided. Also provided are methods of assaying to detect or quantitate bilirubin in a sample, wherein a sample suspected to contain bilirubin is contacted with a diazonium ion compound as disclosed herein, and then the product of the reaction of the diazonium ion and the bilirubin is detected, for example, spectrophotometrically.

In one embodiment, the diazonium ion compounds of Formula I are provided:

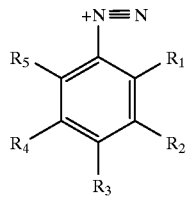

Formula I wherein at least one of $R_1$, $R_2$, $R_3$, $R_4$ or $R_5$ is H, alkyl, sulfonate or nitro, and wherein the compound is capable of reacting with bilirubin in a sample to produce a detectable product.

Preferred are compounds of Formula I wherein:
one of $R_1$, $R_2$, $R_3$, $R_4$ or $R_5$ is C1–C3 alkyl, preferably methyl;
one of $R_1$, $R_2$, $R_3$, $R_4$ or $R_5$ is sulfonate or nitro, preferably nitro; and
the remainder of $R_1$, $R_2$, $R_3$, $R_4$ and $R_5$ are H.

In one preferred embodiment, the diazonium ion is 2-methyl-3-nitroaniline diazonium ion (2-methyl-3-nitro-1-benzenediazonium ion), having the structure:

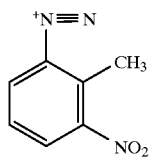

2-methyl-3-nitroaniline diazonium ion

Other preferred compounds include 4-aminotoluene-3-sulfonic acid diazonium ion.

Preferred compounds are diazonium ion compounds which are formed from precursor compounds including an amine group, wherein the precursor amine compounds have a solubility of at least about 0.038 mg/ml in acidic aqueous solutions, e.g., in 100 mM HCl at a pH of about 1.0.

Also provided are reagent compositions including the diazonium ions. The reagent compositions may be in liquid or solid form, and further may include other components, such as buffers, carriers and/or solubilizers. Salts including the diazonium ion and a counteranion also are provided. Preferred salts include tetrafluoroborate, hexafluorophosphate, and metal double salts such as the zinc double chlorides.

Using the assay methods disclosed herein, the total amount of bilirubin in a sample may be quantitated. In another embodiment, the sample includes direct and indirect bilirubin, and the method may further include detecting the concentration of direct and indirect bilirubin in the sample. Thus, the level of direct, indirect, and total bilirubin in a sample may be measured and correlated with the presence or absence of a disease or disorder, for example, of the liver, gall bladder or intestines.

BEST MODE FOR CARRYING OUT THE INVENTION

Figure 1:
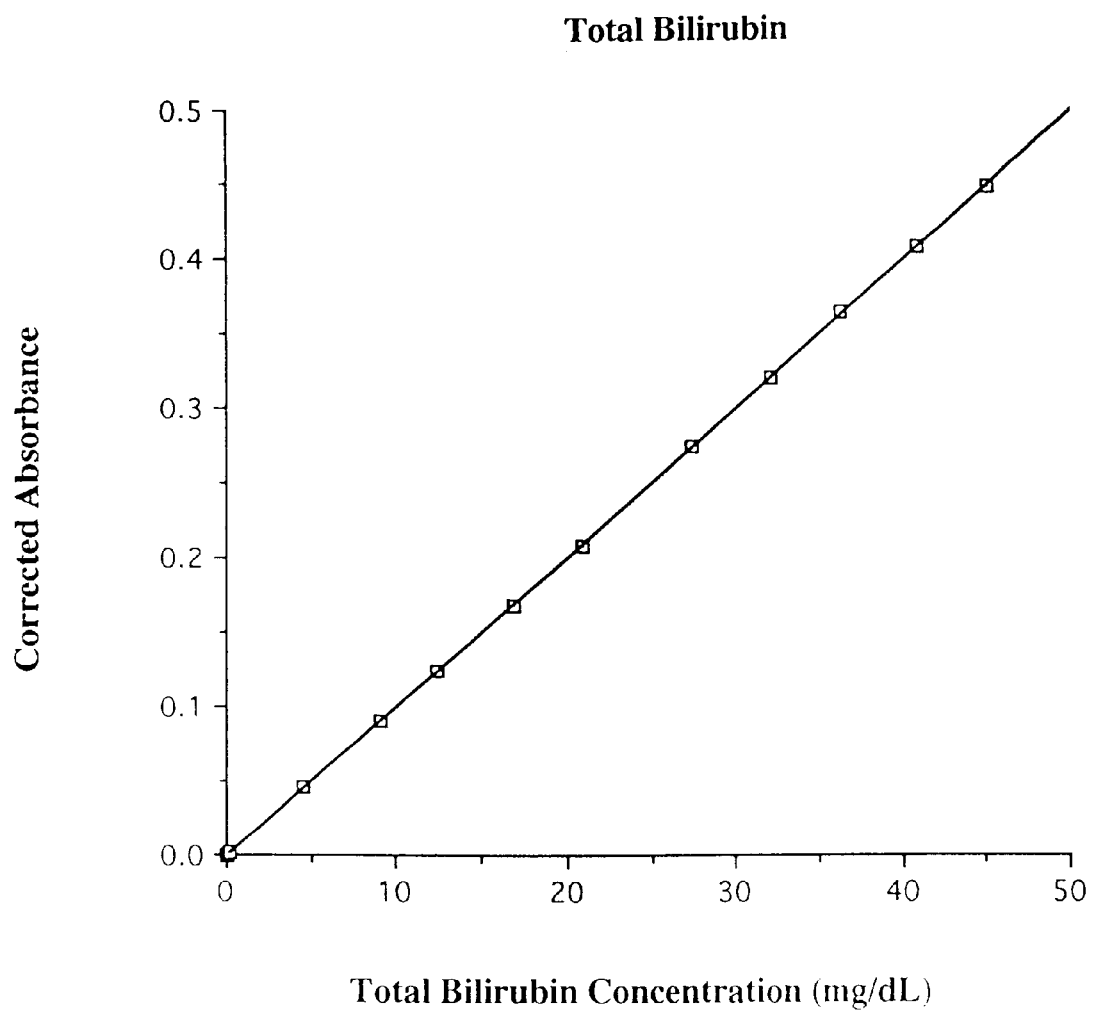
FIG. 1 is a graph of absorbance vs. total bilirubin concentration obtained in a bilirubin assay using 2-methyl-3-nitroaniline diazonium ion.

Diazonium compounds are provided which are useful as assay reagents. In particular, the diazonium compounds are useful in assays for detecting or quantitating bilirubin in a body fluid sample. In one embodiment, diazonium compounds of the general Formula I below are provided:

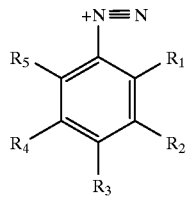

Formula I wherein at least one of $R_1$, $R_2$, $R_3$, $R_4$ or $R_5$ is H, alkyl, sulfonate or nitro, and wherein the compound is capable of reacting with bilirubin in a sample to produce a detectable product. Preferred alkyl groups include C1–C3 alkyl groups including methyl, ethyl and propyl. A particularly preferred alkyl group is methyl.

In a preferred embodiment:
one of $R_1$, $R_2$, $R_3$, $R_4$ or $R_5$ is C1–C3 alkyl, preferably methyl;
one of $R_1$, $R_2$, $R_3$, R4 or $R_5$ is sulfonate or nitro, preferably nitro; and
the remainder of $R_1$, $R_2$, $R_3$, $R_4$ and $R_5$ are H.

Exemplary compounds include 4-aminotoluene-3-sulfonic acid diazonium ion. Other exemplary compounds include the diazonium ions of 2-methyl-4-nitroaniline, 2-methyl-5-nitroaniline, 2-methyl-5-nitroaniline hydrate, 2-methyl-6-nitroaniline, and 5-methyl-2-nitroaniline.

In one preferred embodiment, the compound is the diazonium ion of 2-methyl-3-nitroaniline shown below:

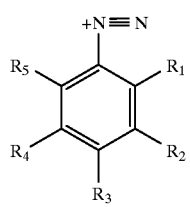

2-methyl-3-nitroaniline diazonium ion

The compounds advantageously may be used in assays to detect and quantitate bilirubin in a body fluid sample, such as a serum sample. Preferred compounds of Formula I are those which are thermally stable and have a long shelf life. The compounds may be used to identify disease states such as impaired function of the liver, gall bladder or intestinal tract.

Preferred compounds are diazonium ion compounds which are formed from precursor compounds including an amine group, wherein the precursor compounds have a solubility of at least about 0.038 mg/ml, or optionally at least about 0.5 mg/ml, or preferably at least about 2.0 mg/ml in acidic aqueous solutions, e.g., 100 mM HCl, at a pH of about 1.0. For example, 2-methyl-3-nitroaniline, the precursor of 2-methyl-3-nitroaniline diazonium ion, has a solubility of about 2.3 mg/ml in 100 mM HCl, at a pH of about 1.0.

Synthesis of Diazonium Compounds

The diazonium compounds may be synthesized using methods for generating diazonium cations known in the art. Heinrich Zollinger, "Diazo Chemistry I, Aromatic and Heteroaromatic Compounds," VCH Publishers, New York, N.Y., 1994, Chapter 2. In general, the diazonium ions may be prepared by diazotization of the free arylamine using sodium nitrite and an acid such as hydrochloric acid to produce the desired diazonium salt. The desired anion for the diazonium salt may be provided by including a salt of the anion in the diazotization reaction mixture. For example, if sodium hexafluorophosphate is included in the reaction mixture, the hexafluorophosphate diazonium salt is produced. Alternatively, the tetrafluoroborate salt may be produced. Other salts include the metal double salts, in particular the zinc double chlorides, $ZnCl_4^{2-}$. Thus, compositions within the scope of the invention include salts of the diazonium cations.

An exemplary synthesis is the synthesis of 2-methyl-3-nitroaniline diazonium ion (2). In this embodiment, 2-methyl-3-nitroaniline (1) is converted to the diazonium ion (2) by reaction with sodium nitrite in an acidic aqueous medium. The reaction is illustrated in Scheme I below. The 2-methyl-3-nitroaniline diazonium ion (2) is capable of reacting with bilirubin to form a detectable product, and is thus useful in assays for detecting and quantitating bilirubin in a sample. The 2-methyl-3-nitroaniline diazonium ion precursor, 2-methyl-3-nitroaniline, also advantageously has good solubility in aqueous systems. 2-methyl-3-nitroaniline has a solubility of at least about 2.3 mg/ml in 100 mM HCl at a pH of about 1.0.

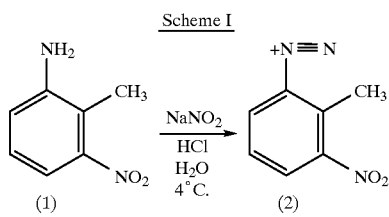

Scheme I

Reagent Compositions

Reagent compositions including the diazonium ion compounds for use in assays may be provided in a variety of forms including solutions and solid forms.

In one embodiment, the reagent composition is in the form of a stable liquid reagent solution. In a preferred embodiment, the diazonium ion compound is provided in an aqueous acidic solution, at a preferred concentration of about 0.25 mM to 15 mM, at pH less than about 7, preferably about pH 0.5 to 2. The solid or liquid reagent composition further optionally may include other added materials, such as buffers or solubilizers.

Buffer systems which may be used include citric acid/tris-(hydroxymethyl)-aminomethane, citric acid/aqueous sodium hydroxide solution, acetic acid/aqueous sodium hydroxide solution, acetic acid/sodium acetate, potassium hydrogen phthalate/aqueous sodium hydroxide solution or phosphate buffers. Preferred buffer systems include an acetate, sodium acetate/acetic acid system.

Solutions used in the bilirubin assays can include solubilizers and detergents. Exemplary solubilizers include dimethylformamide, dimethyl sulphoxide, tetrahydrofuran, dioxan and various glycols such as polyethylene glycol. Other exemplary solubilizers include a non-ionic detergent, such as polyoxyethylated octyl phenol (e.g., Triton® X 100, Rohm & Haas, Philadelphia, Pa., which can be added at a concentration of, for example, from about 0.1 to 1.0% (w/v). Further examples of non-ionic detergents which can be used include polyoxyethylene sorbitan monolaurate (e.g., Tween®20, ICI, Wilmington, Del., polyoxyethylene sorbitan monopalmitate (Tween® 40, ICI, Wilmington, Del., and polyglycol ether surfactants such as Tergitol® 15-S-30 (Union Carbide Corp., Houston, Tex. Ionic detergents also may be used, such as alkyl betaine (Empigen BB, Albright and Wilson, Ashland, Va). In one embodiment, aqueous test solutions including a solubilizer are provided, including about 1 to 13% (w/v) solubilizer, wherein the pH is less than 7, preferably about pH 0.5 to 7.

The diazonium ion compound may be provided in a formulation in combination with any of a variety of materials such as a carrier, buffer and/or solubilizer. Suitable carriers include water, preferably an acidic aqueous solution. Salts including the diazonium ion compound and a counteranion also are provided. Preferred salts include tetrafluoroborate, hexafluorophosphate and the metal double salts such as the zinc double chlorides.

Reagent compositions also may include the diazonium ion compound or salt thereof and an acid. The diazonium ion compound or salt thereof may be stored at an acid pH. Where the reagent composition is in the form of an aqueous solution, useful acids include mineral acids, such as hydrochloric acid and sulfuric acid. For a dry reagent composition, acids which are solid when anhydrous may be used, such as malic, sulfosalicylic, tartaric, succinic, cyclohexanesulfamic, p-toluenesulfonic and citric acid. If the reagent composition includes a carrier, an acid may be included which does not degrade the carrier matrix. Alternatively, a combination of materials which are capable of generating the acid in situ on contact with water may be included, such as a solid adduct of a Friedel Crafts salt and an organic Lewis base with a weak acid such as an organic acid as described in U.S. Pat. No. 3,814,586. The presence of the acid can promote the coupling of the diazonium ion salt with bilirubin. The amount of acid in the reagent may vary. For example, acids may be added to an aqueous solution of the diazonium ion compound in an effective amount to provide a reagent solution having a pH less than about 7, preferably about pH 0.5 to 2. The acid also may be present in a dry analytical element used in the assay.

The reagent composition including the diazonium ion compound may be prepared in a variety of solid forms, or combination of forms. The reagent composition may be prepared as a powder or tablets which are reconstituted with water or suitable diluent to produce a reagent solution. Techniques for making solid forms of reagent compositions and materials such as fillers and binders, known in the art, may be used.

A dry analytical element also may be used including the reagent composition on a suitable support. Contact of the support with a sample can dissolve the reagent composition and then the presence of bilirubin in the sample is detected. Dry analytical elements may be formulated which comprise a carrier matrix impregnated with the reagent composition. Useful carrier materials are insoluble and maintain structural integrity when exposed to water or physiological fluids such as serum or urine. Exemplary matrixes include paper, cellulose, wood, glass fiber, and woven and nonwoven fabrics. For example, a dry analytical element may be made by applying a solution containing the reagent composition to the matrix and then drying.

Assays

In one embodiment, reagent compositions including stable diazonium ion compounds are provided in solution which may be used in an assay to detect or quantitate bilirubin in a body fluid sample. The bilirubin in the sample reacts with the diazonium ion compound to produce azobilirubin in an acidic solution which absorbs maximally at about 540 nm. In alkaline media the chromophore shifts to, for example, about 600 nm. The reaction product can be detected using a spectrophotometer or other analyzer capable of measuring absorbance at the desired wavelength. For example, the Hitachi line of analyzers may be used (Boehringer Mannheim Diagnostics, Inc., Indianapolis, Ind.). The levels of bilirubin in a blood, plasma or serum sample thus can be accurately measured using the diazonium compounds.

For many diagnostic applications, it is important to quantitate direct bilirubin in addition to total bilirubin. Methods for quantitating direct, indirect and total bilirubin using diazo reagents are developed in the art. See for example, Lott and Doumas, *Clin. Chem.*, 39:641–647 (1993); and Doumas and Wu, *Critical Reviews in Clinical Laboratory Sciences*, 28:415–445 (1991).

To quantitate total bilirubin, the diazonium compound is reacted with a sample suspected to contain bilirubin in the presence of an accelerator such as caffeine. After the reaction is complete (about 10 minutes) the azobilirubin product is detected spectrophotometrically by absorbance at about 540 nm. Alternatively, the solution may be changed to alkaline by, for example, the addition of alkaline tartrate reagent, and the absorbance at about 598 nm may be measured. Other accelerating reagents (or promoters) which can be used, which promote the formation of diazobilirubin, include dyphylline, sodium acetate, sodium benzoate and gum arabic. The absorbance is detected using a sample blank containing the assay components without the bilirubin sample. Bilirubin from the National Institute for Standards and Technology (NIST), SRM 916a, may be used for preparing standard solutions for calibration of the bilirubin assay.

In some diagnostic applications, it is important to be able to detect direct bilirubin without reaction of the diazonium compound with the unconjugated bilirubin. In general, the direct reacting bilirubins (bilirubin mono and diglucuronide and delta bilirubin) are reacted with diazonium ion in the absence of an accelerator. In the assay, the diazonium ion compound is combined with the bilirubin sample, such as a serum sample. Other components of the assay solution may include water, buffers, stabilizers and HCl. At the end of the coupling (about 10 minutes), the absorbance of the azopigment is measured near 540 nm, or after adding a base such as alkaline tartrate, near 598 nm. The pH is preferably as low as possible to prevent the reaction of the unconjugated bilirubin. To keep unconjugated bilirubin from reacting, the serum sample may be diluted with HCl (for example 100 mmol/L) and incubated for at least about 5 minutes before adding diazo reagent.

Preferably, the assay is conducted in aqueous systems. In an exemplary assay for total bilirubin in a sample, such as a plasma or serum sample, two assay formulations are provided, an acidic solubilizer formulation (referred to herein as a Total Bilirubin R1 Formulation), and a reagent formulation (referred to herein as a Total Bilirubin R2 Formulation), which includes the diazonium ion compound (See Tables 1 and 2). The assay described herein may be modified, by for example, modification of components of the R1 and R2 Formulation, and incubation times or temperatures. The following assay conditions and formulations are provided by way of example.

In the assay, 4–6 $\mu$l of the sample is added to 250 $\mu$l of Total Bilirubin R1 Formulation, and mixed (a ratio of about 1:62 to about 1:42 sample:R1 Formulation). If the concentration of bilirubin in the sample is found to be greater than 35 mg/dL, the sample can be diluted 1+1 with physiological saline and reassayed. The mixture is incubated, for example, at 25, 30 or 37° C. for about 3 to 5 minutes. A sample blank is included for each patient sample, standard and control. After about 5 minutes, 65 $\mu$l of the acidic Total Bilirubin R2 Formulation is added (a volume equal to about 13/50 of the volume of the R1 Formulation). The solution is mixed, and the absorbance at about 540 nm is detected using a spectrophotometer, preferably before about 10 minutes after the end of the incubation reaction. The absorbance is compared with a standard of known total bilirubin concentration, and the concentration of the sample thereby determined.

Nonlimiting examples of Formulations for the Total Bilirubin assay are shown below in Tables 1 and 2:

TABLE 1

Total Bilirubin R1 Formulation

| Component | Concentration |
|---|---|
| alkyl betaine (Empigen BB) | 4–13% (w/v), e.g., 11% (w/v) |
| Potassium Iodide | 0–12.5 mM, e.g., 12.5 mM |
| Antifoam FG-10 Emulsion | 1500 ppm |
| Sodium Acetate.3H$_2$O | 50-150 mM, e.g., 85 mM |
| Sulfamic Acid | 50-200 mM, e.g., 110 mM |

TABLE 2

Total Bilirubin R2 Formulation

| Component | Concentration |
|---|---|
| HCl | 50–500 mM, e.g., 100 mM |
| 2-methyl-3-nitroaniline | 1–15 mM, e.g., 3 mM |
| Sodium nitrite | 1–20 mM, e.g., 8 mM |
| Sulfamic Acid | 1–25 mM, e.g., 5 mM |

The components of the Total Bilirubin R1 and R2 Formulations may be obtained from commercial suppliers. For example, alkyl betaine (C12–C14 alkyl betaine, Empigen BB) may be obtained from Albright & Wilson, (Ashland, Va.); potassium iodide, sulfamic acid, and HCl are available from J. T. Baker (Phillipsburgh, N.J.); Antifoam FG-10 emulsion (an emulsion including polydimethylsiloxane) is available from Dow Corning (Midland, Mich.); sodium acetate.3H$_2$O is available from Fisher Scientific (Itaska, Ill.); 2-methyl-3-nitroaniline is available from Aldrich Chemical Co., St. Louis, Mo.; and sodium nitrite is available from Sigma Chemical Company, St. Louis, Mo.

The above formulations all are made up in water. Upon combining the components to form the R2 Formulation, the nitrite reacts with the acid to form nitrous acid which subsequently reacts with the 2-methyl-3-nitroaniline, to form the 2-methyl-3-nitroaniline diazonium ion. Thus, after the reaction, nitrite and 2-methyl-3-nitroaniline substantially are no longer present in the R2 Formulation.

Direct Bilirubin also may be quantitated in a sample. In an exemplary assay for direct bilirubin in a sample, such as a plasma or serum sample, two assay formulations again are provided, an acidic formulation (referred to herein as a Direct Bilirubin R1 Formulation), and a reagent formulation (referred to herein as a Direct Bilirubin R2 Formulation), which includes the diazonium ion compound (see Tables 3 and 4 below). While the components of the R1 and R2 Formulation and incubation times may be designed and optimized using knowledge of bilirubin assays developed in the art, the following assay conditions and formulations are provided by way of example.

In an exemplary assay for direct bilirubin concentration in a serum sample, 6 μl of the sample is added to 250 μl of Direct Bilirubin R1 Formulation, and mixed (a ratio of about 1:42 sample:R1 Formulation). If the concentration of bilirubin in the sample is greater than 20 mg/dL, the sample can be diluted 1+1 with physiological saline and reassayed. The mixture is incubated at 25, 30 or 37° C. for about 30 seconds to 5 minutes. A sample blank is included for each patient sample, standard and control. After 5 minutes, 65 μl of the Direct Bilirubin R2 Formulation is added (a volume equal to 13/50 of the volume of the Direct Bilirubin R1 formulation). The solution is mixed, and the absorbance at about 540 nm is detected using a spectrophotometer, preferably before about 10 minutes after the end of the incubation reaction. The absorbance is correlated with a standard curve prepared using samples of known bilirubin concentration, thereby permitting the determination of direct bilirubin concentration in the sample.

Nonlimiting examples of Formulations for the Direct Bilirubin assay are shown below in Tables 3 and 4:

TABLE 3

Direct Bilirubin R1 Formulation

| Component | Concentration |
|---|---|
| Betaine monohydrate | 1–8% (w/v), e.g., 2% (w/v) |
| Thesit ® | 0.05–0.3% (w/v), e.g., 0.2% (w/v) |
| Potassium Iodide | 0.1–12 mM, e.g., 2 mM |
| Sodium Acetate.3H$_2$O | 50–150 mM, e.g., 85 mM |
| Sulfamic Acid | 50–300 mM, e.g., 200 mM |

TABLE 4

Direct Bilirubin R2 Formulation

| Component | Concentration |
|---|---|
| HCl | 100 mM |
| 2-methyl-3-nitroaniline | 0.25–12 mM, e.g., 3 mM |
| Sodium Nitrite | 8–11 mM, e.g., 8 |
| Sulfamic Acid | 5 mM |

The components of the Direct Bilirubin Formulations can be obtained from commercial suppliers. For example, betaine monohydrate and sodium nitrite may be obtained from Sigma Chemical Co. (St. Louis, Mo.). Thesit® (dodecylpoly(ethyleneglycolether)$_n$) can be obtained from Boehringer Mannheim Corporation (Indianapolis, Ind.); potassium iodide, sulfamic acid and HCl may be obtained from J. T. Baker (Phillipsburgh, N.J.); sodium acetate 3H$_2$O is available from Fisher Scientific (Itaska, Ill.); and 2-methyl-3-nitroaniline is available from Aldrich Chemical Co. (St. Louis, Mo.).

The above formulations are all made up in water. As noted above, upon combining the components of the R2 Formulation, the nitrite reacts with the acid to form nitrous acid which subsequently reacts with the 2-methyl-3-nitroaniline, to form the 2-methyl-3-nitroaniline diazonium ion. Thus, after the reaction, nitrite and 2-methyl-3-nitroaniline are substantially no longer present in the Formulation.

Advantages and Properties of the Diazonium Ions

Preferred diazonium ion compounds within the scope of the invention are compounds capable of reacting with bilirubin to form a product which can be detected, for example spectrophotometrically. Compounds which are highly reactive with bilirubin are especially preferred.

Also preferred are diazonium ion compounds as defined herein which are thermally stable. As used herein, "thermally stable" refers to compounds and/or reagent formulations containing the compounds, wherein about 60% of the compound remains undecomposed and active after being subjected to a temperature of about 42° C. for at least one day. The diazonium compounds preferably are stable enough to meet thermal requirements for international shipping. Subsequent to thermal stressing of the reagent, it preferably also has sufficient levels, on the order of at least about 60% of initial, of active components to provide a shelf-life of at least 12 months at 4° C.

In a preferred embodiment, the compounds also substantially do not react with potentially interfering compounds in a body fluid or other sample, such as hemoglobin or indican. Preferably, the compound permits accurate measurement of bilirubin even in a sample containing up to 2000 mg/dL of hemoglobin. In another embodiment, the compound permits accurate measurement of bilirubin even in a sample containing up to 10 mg/dL indican. Also preferred are compounds formed from amine precursors which are soluble in an aqueous system. A problem with prior art compounds has been low solubility in aqueous systems.

One example of a preferred diazonium ion compound is 2-methyl-3-nitroaniline diazonium ion. This compound does not substantially react with interfering compounds in a serum or other body fluid sample. This compound permits the accurate measurement of bilirubin in samples which are grossly hemolyzed, which contain extremely high hemoglobin concentrations, for example, as high as 2000 mg dL$^{-1}$. Other interfering compounds, such as indican, also do not react significantly with 2-methyl-3-nitroaniline diazonium ion. Bilirubin can be assayed even in samples with indican levels, for example, as high as 10 mg dL$^{-1}$. This enables the assay of a wide range of samples.

The 2-methyl-3-nitroaniline diazonium ion also is highly reactive with bilirubin, and is thermally stable. This compound is stable enough to meet thermal requirements for international shipping. The 2-methyl-3-nitroaniline diazonium ion withstands relatively high temperatures (42° C.) for at least one day, with decomposition of less than 40%. Subsequent to thermal stressing of the compound, for example in liquid reagent form as described in detail above, it has sufficient levels of active components to provide a shelf-life of at least 12 months at 4° C.

Arrhenius estimates of stability at 4° C. indicate that the 2-methyl-3-nitroaniline diazonium ion is about 2–2.5 times more stable than the sulfanilamide diazonium ion currently used in the quantitation of bilirubin. Thus, this reagent meets rigorous thermal stressing requirements and retains sufficient levels of active component to maintain a shelf-life of at least 12 months at 4 ° C. The 2-methyl-3-nitroaniline diazonium ion also is highly soluble in water or other aqueous systems.

Thus, the 2-methyl-3-nitroaniline diazonium ion has many advantages as a bilirubin assay reagent. The compound is thermally stable, is highly reactive with bilirubin, and permits accurate measurements even in the presence of high levels of hemoglobin, or other interfering compounds, such as indican. The use of this compound permits the assay of a wide range of sample types, including body fluids such as serum, urine, and plasma. Assay of the levels of either total bilirubin or direct bilirubin in a body fluid sample thus permits the detection and diagnosis of a variety of metabolic disturbances, abnormal states, and diseases associated with changes in levels of either total, direct or indirect bilirubin including those affecting the liver, gall bladder and intestines.

The invention will be further understood by the following nonlimiting examples.

EXAMPLES

Example 1

Preparation of 2-Methyl-3-Nitroaniline Diazonium ion and Assay for Bilirubin The quantity of direct and total bilirubin in a serum or plasma sample is detected. 2-methyl-3-nitroaniline diazonium ion is generated in a formulation for the total bilirubin assay (Total Bilirubin R2 Formulation) and in a formulation for the direct bilirubin assay (Direct Bilirubin R2 Formulation). Additionally, acidic solutions are provided for the total bilirubin assay (Total Bilirubin R1 Formulation) and for the direct bilirubin assay (Direct Bilirubin R1 Formulation). The components used to form the Formulations, which are made up in water, are shown below in Tables 5–8.

TABLE 5

Total Bilirubin R1 Formulation

| Component | Concentration | Supplier |
|---|---|---|
| Empigen BB | 11.00% (w/v) | Albright & Wilson |
| Antifoam FG-10 Emulsion | 1500 ppm | Dow Corning |
| Sodium Acetate.3H$_2$O | 85 mM | Fisher Scientific |
| Sulfamic Acid | 110 mM | J. T. Baker |

TABLE 6

Total Bilirubin R2 Formulation

| Component | Concentration | Supplier |
|---|---|---|
| HCl | 100 mM | J. T. Baker |
| 2-methyl-3-nitroaniline | 3 mM | Aldrich |
| Sodium nitrite | 8 mM | Sigma |
| Sulfamic Acid | 5 mM | J. T. Baker |

TABLE 7

Direct Bilirubin R1 Formulation

| Component | Concentration | Supplier |
|---|---|---|
| Betaine monohydrate | 2.00% (w/v) | Sigma |
| Thesit ® | 0.20% (w/v) | Boehringer Mannheim |
| Potassium Iodide | 2 mM | J. T. Baker |
| Sodium Acetate.3H$_2$O | 85 mM | Fisher Scientific |
| Sulfamic Acid | 200 mM | J. T. Baker |

TABLE 8

Direct Bilirubin R2 Formulation

| Component | Concentration | Supplier |
|---|---|---|
| HCl | 100 mM | J. T. Baker |
| 2-methyl-3-nitroaniline | 3 mM | Aldrich |
| Sodium Nitrite | 8 mM | Sigma |
| Sulfamic Acid | 5 mM | J. T. Baker |

For the Total and Direct Bilirubin R2 Formulations, since the nitrite reacts with the acid to form nitrous acid, which subsequently reacts with the 2-methyl-3-nitroaniline to form the 2-methyl-3-nitroaniline diazonium ion, nitrite as such substantially no longer exists in the reagent, nor does the 2-methyl-3-nitroaniline. The R2 Formulations after mixing of the components therein are stable for at least about 18 months at 4° C.

To form the R2 solution, 2-methyl-3-nitroaniline is dissolved in 100 mM HCl at room temperature. The solution is cooled to ~4° C. The appropriate amount of solid sodium nitrite is slowly added, while keeping the solution cold, and permitting all the nitrite to completely dissolve. The appropriate amount of solid sulfamic acid is added to the solution, while keeping the solution cold, and ensuring complete dissolution of the sulfamic acid.

The assay is conducted using a clinical analyzer, such as the Boehringer Mannheim Diagnostics, Inc., (Indianapolis, Ind.) Hitachi® series of clinical analyzers, H717, H917, or H747. The calibration standard is Precical (Boehringer Mannheim; Indianapolis, Ind.), a commercially available calibrator having defined level of bilirubin. Serum based bilirubin sample control materials having known concentrations of bilirubin which also may be used are Precitrol-A (PTA), an abnormal control material, and Precitrol-N (PTN), a normal control material. The blank or zero calibrator used is saline.

In the assay, 6 μL of the sample and 250 μL R1 Formulation are incubated for 5 minutes at 37° C. Subsequently, 65 μL R2 Formulation is added and the solution incubated for 5 minutes at 37° C. The absorbance at 546 nm 5 minutes after addition of R2 Formulation is measured and correlated with the standard to determine bilirubin concentration. The Hitachi analyzer also subtracts absorbance at a secondary wavelength, for example, of 660 or 700 nm.

FIG. 1 illustrates a plot of absorbance vs. total bilirubin concentration obtained using this method to analyze normal human serum based samples spiked with different concentrations of pure unconjugated bilirubin (NIST-traceable). The Hitachi 717 Clinical Analyzer was used for analysis of the samples after calibration with Precical. The corrected absorbance on the y-axis corresponds to the sample absorbance minus the absorbance of the blank (saline). This plot illustrates the concentration obtained from the sample absorbance related to the calibrator absorbance as well as the linearity of the method.

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention.

We claim:

1. A reagent composition for detecting bilirubin comprising a solubilizer and 2-methyl-3-nitroaniline diazonium ion having the structure:

2. The reagent composition of claim 1 further comprising a buffer system.

3. The reagent composition of claim 2 wherein the buffer system is selected from the group consisting of citric acid/tris-(hydroxymethyl)-aminomethane, citric acid/aqueous sodium hydroxide solution, acetic acid/aqueous sodium hydroxide solution, acetic acid/sodium acetate, potassium hydrogen phthalate/aqueous sodium hydroxide solution and phosphate buffers.

4. The reagent composition of claim 1 comprising an aqueous solution of 2-methyl-3-nitroaniline diazonium ion.

5. The reagent composition of claim 4, wherein the pH of the solution is less than about 7.

6. The reagent composition of claim 4 comprising about 0.25–15 mM diazonium ion, wherein the pH of the solution is about 0.5 to 7.

7. The reagent composition of claim 4, wherein the pH of the solution is about 0.5 to 2.

8. The reagent composition of claim 7 comprising about 0.25–15 mM 2-methyl-3-nitroaniline diazonium ion.

9. The reagent composition of claim 4, wherein the concentration of the solubilizer is about 1–13% (w/v).

10. The reagent composition of claim 1 wherein the solubilizer is a detergent.

11. The reagent composition of claim 10, wherein the detergent is selected from the group consisting of polyoxyethylated octyl phenol, polyoxyethylene sorbitan monolaurate, polyoxyethylene sorbitan monopalmitate and polyglycol ether surfactants and alkyl betaine.

12. The reagent composition of claim 1 wherein the composition comprises a salt of the diazonium ion selected from the group consisting of a tetrafluoroborate, a hexafluorophosphate and a metal double salt.

13. The reagent composition of claim 1, wherein the solubilizer is selected from the group consisting of dimethylformamide, dimethyl sulphoxide, tetrahydrofuran, dioxan and a glycol.

14. A reagent composition for detecting bilirubin comprising 2-methyl-3-nitroaniline diazonium ion and a carrier matrix.

15. The reagent composition of claim 14, wherein the carrier matrix is selected from the group consisting of paper, cellulose, wood, glass fiber and fabrics.

16. A reagent composition for detecting bilirubin comprising an aqueous solution of about 0.25 to 15 mM 4-aminotoluene-3-sulfonic acid diazonium ion and a solubilizer, at a pH of about 0.5 to 7.

17. A reagent composition for detecting bilirubin comprising an aqueous solution at a pH of about 0.5 to 7 of about 0.25 to 15 mM of 2-methyl-4-nitroaniline diazonium ion, wherein the solution further comprises a solubilizer.

18. A method of assaying for bilirubin in a sample, the method comprising:
 a) contacting a sample suspected to contain bilirubin with 2-methyl-3-nitroaniline diazonium ion having the structure:

b) permitting the diazonium ion to react with bilirubin in the sample to produce a detectable product; and
 c) detecting the product.

19. The method of claim 18 wherein the product is detected spectrophotometrically.

20. The method of claim 18, further comprising quantitating the bilirubin in the sample.

21. The method of claim 20, wherein the sample includes direct and indirect bilirubin, wherein the method further comprises detecting the concentration of direct and total bilirubin in the sample.

22. The method of claim 21, wherein the method comprises detecting a disease or disorder of the liver, gall bladder or intestines based on the detected concentrations of the direct and total bilirubin.

23. The method of claim 18, wherein step a) comprises contacting the sample with an aqueous solution comprising about 0.25–15 mM 2-methyl-3-nitroaniline diazonium ion, wherein the pH of the solution is about 0.5 to 7.

24. The method of claim 23 wherein step c) comprises contacting the sample after step b) with an acidic solution and detecting the absorbance of the product.

25. The method of claim 18, wherein the diazonium ion contacted with the sample is in an aqueous solution comprising a buffer system.

26. The method of claim 25, wherein the buffer system is selected from the group consisting of citric acid/tris-(hydroxymethyl)-aminomethane, citric acid/aqueous sodium hydroxide solution, acetic acid/aqueous sodium hydroxide solution, acetic acid/sodium acetate, potassium hydrogen phthalate/aqueous sodium hydroxide solution and phosphate buffers.

27. The method of claim 18, wherein the diazonium ion contacted with the sample is in an aqueous solution comprising a solubilizer selected from the group consisting of dimethylformamide, dimethyl sulphoxide, tetrahydrofuran, dioxan and a glycol.

28. The method of claim 18, wherein the diazonium ion contacted with the sample is in an aqueous solution comprising a solubilizer, wherein said solubilizer is a detergent.

29. The method of claim 28, wherein the detergent is selected from the group consisting of polyoxyethylated octyl phenol, polyoxyethylene sorbitan monolaurate, polyoxyethylene sorbitan monopalmitate and polyglycol ether surfactants and alkyl betaine.

30. A method of assaying for bilirubin in a sample, the method comprising:
 a) contacting a sample suspected to contain bilirubin with 4-aminotoluene-3-sulfonic acid diazonium ion;
 b) permitting the diazonium ion to react with bilirubin in the sample to produce a detectable product; and
 c) detecting the product.

31. A reagent composition for detecting bilirubin comprising a solubilizer and an aqueous solution of a compound selected from the group consisting of 2-methyl-6-nitroaniline diazonium ion and 5-methyl-2-nitroaniline diazonium ion,
 wherein the concentration of compound is about 0.25 to 15 mM, and wherein the pH of the solution is about 0.5 to 7.

32. A reagent composition comprising 2-methyl-3-nitroaniline diazonium ion and bilirubin.

33. A reagent composition for detecting or quantitating bilirubin comprising: 50–500 mM HCl; 1–15 mM 2-methyl-3-nitroaniline; 1–20 mM sodium nitrite; and 1–25 mM sulfamic acid.

34. A reagent composition for detecting or quantitating bilirubin comprising: 100 mM HCl; 0.25–12 mM 2-methyl-3-nitroaniline; 8–11 mM sodium nitrite; and 5 mM sulfamic acid.

35. A method of assaying for bilirubin in a sample, the method comprising:
 a.) contacting a sample suspected to contain bilirubin with a reagent composition comprising a solubilizer and a diazonium ion compound selected from the group consisting of 2-methyl-6-nitroaniline diazonium ion and 5-methyl-2-nitroaniline diazonium ion;
 b.) permitting the compound to react with bilirubin in the sample to produce a detectable product; and
 c.) detecting the product.

* * * * *